USOO5626760A

United States Patent [19]
Pouchoulin

[11] Patent Number: 5,626,760
[45] Date of Patent: May 6, 1997

[54] MULTIFUNCTION DEVICE FOR THE TREATMENT OF BLOOD

[75] Inventor: Dominique Pouchoulin, Tramoyes, France

[73] Assignee: Hospal Industries (S.A.), Meyzieu Cedex, France

[21] Appl. No.: 466,687

[22] Filed: Jun. 6, 1995

[30] Foreign Application Priority Data

Jun. 20, 1994 [FR] France .................. 94 07752

[51] Int. Cl.$^6$ .............. B01D 61/00; B01D 63/00
[52] U.S. Cl. .............. 210/645; 210/321.75; 210/321.84; 210/500.43; 210/500.21; 210/500.27
[58] Field of Search .................. 210/321.6, 321.72, 210/321.75, 321.84, 321.79, 321.77, 500.23, 500.27, 500.43, 645, 647, 500.21; 264/165; 428/398; 604/6; 530/351; 521/142

[56] References Cited

U.S. PATENT DOCUMENTS

| | | | |
|---|---|---|---|
| 4,056,467 | 11/1977 | Christen et al. | 210/500.43 |
| 4,238,340 | 12/1980 | Markley et al. | 210/321.77 |
| 4,749,619 | 6/1988 | Angleraud | 428/398 |
| 4,834,882 | 5/1989 | Kataoka et al. | 210/321.6 |
| 4,925,534 | 5/1990 | Kataoka et al. | 210/647 |
| 4,950,395 | 8/1990 | Richalley | 210/321.72 |
| 5,145,583 | 9/1992 | Angleraud et al. | 210/500.43 |
| 5,236,592 | 8/1993 | Dejardin et al. | 210/646 |
| 5,436,275 | 7/1995 | Kawasaki et al. | 521/142 |

FOREIGN PATENT DOCUMENTS 2758679   7/1979   Germany.

*Primary Examiner*—Ana Fortuna
*Attorney, Agent, or Firm*—Millen, White, Zelano, & Branigan, P.C.

[57] ABSTRACT

The present invention relates to a multifunction device for treatment of blood and more particularly for extrarenal purification by extracorporeal circulation of blood. A device is proposed including a semipermeable separator component which is:

a) active in adsorption and has at least one of the adsorption capacities below a1: adsorption of TNF-α greater than or equal to approximately 600 ng a2: adsorption of complement factor D greater than or equal to approximately 30 mg a3: adsorption of interleukin 1-β greater than or equal to approximately 300 ng b) has a urea clearance greater than or equal to approximately 20 ml/min for rates of blood flow, of dialysis liquid flow and of ultrafiltration equal respectively to approximately 100 ml/min, 33 ml/min and 0 ml/min.

c) has an ultrafiltration coefficent in the presence of blood greater than approximately 5 ml/(h.mmHg).

d) the volume of compartment in the device intended for circulation of blood is less than or equal to approximately 150 ml.

29 Claims, 3 Drawing Sheets

MULTIFUNCTION DEVICE FOR THE TREATMENT OF BLOOD

SUMMARY OF THE INVENTION

The invention relates to a multifunction device for the treatment of blood and more particularly for extrarenal purification by extracorporeal circulation of blood.

Various methods can be employed for removing impurities contained in the blood of a patient.

Haemoperfusion: according to this method, the blood to be treated flows through a sorbent such as activated charcoal, which retains impurities by absorption or by adsorption. In order to avoid damaging the blood, it is common practice to cover the sorbent with an impurity-permeable layer, compatible with blood, which prevents direct contact.

Haemofiltration and haemodialysis: these two functions are traditionally present in an artificial kidney.

In the case of haemodialysis, a membrane separates a flow of blood from a flow of dialysate; impurities contained in the blood to be treated diffuse through the membrane towards the dialysate and are thus removed.

In the case of haemofiltration, setting up of a pressure difference on both sides of the membrane forces pert of the blood to pass through it. The fraction which has passed through the filter, called the permeate or ultrafiltrate, contains molecules having a given maximum size (permeability limit of the membrane) but none of the elements figuring in the blood. The filtrate can then be purified (for example by passing over activated charcoal) before being reintroduced into the body of the patient. It is also possible, and more usual, to compensate for the extracorporeal liquid loss and the electrolyte loss for the patient by means of a substitute solution.

These various methods, the effectiveness of which is no longer questioned, are implemented by provision of various types of devices in hospital environments.

In the German Patent Application published before examination under No. 2,758,679, a device is proposed for treatment of blood, which is of the "membrane" type, the active element of which employs a layer of at least one sorbent sandwiched by two semipermeable membranes.

It is thus possible to integrate two of the blood treatment methods, haemperfusion and haemofiltration, in a single apparatus. A fraction of the blood is forced as a filtrate, by application of a pressure gradient, through the three layers of materials: blood-side membrane, sorbent layer, filtrate-side membrane. The filtrate is purified by passing through the intermediate layer; impurities are absorbed by the said layer. The filtrate-side membrane also retains impurities.

British Patent Application No. 2,083,761 proposes a device comprising at least one haemodialysis unit and at least one haemoperfusion unit, which are mounted in series.

The dialysis unit may include hollow fibres; the haemoperfusion unit is filled with an absorbent substance. The two units connected in series constitute separate equipment items of the device in question.

American Patent No. 5,194,157 proposes installation for purification of blood, comprising a haemofiltration element mounted in series with a haemodialysis element, as well as a compensator and a regenerator.

These various types of devices all have at least the following drawback: as soon as it is desired to make them fulfil more than one function, it is necessary to resort to several separate materials and, most often, to several elements or units which are physically separate even if these elements are interconnected.

Furthermore, a very marked need is felt to provide hospital environments with a multifunction device which has a relatively simple design and is relatively simple to use, in order to allow the treatment of so-called "acute" patients who have momentarily lost all or some of their physiological functions, in particular renal functions, following an accident, a surgical operation or a septic or endotoxic shock, for example.

This device should make it possible, in particular, to carry out the following treatments: prophylactic treatment of patients undergoing a septic shock, in the early phase (removal of excess water, of TNF-$\alpha$ (tumor necrosis factor) and interleukin 1-$\beta$); treatment of patients having undergone a renal transplant and subjected to an immunosuppressor of type OKT3 (removal of excess water and TNF-$\alpha$); treatment of patients having undergone cardiac surgery, in the blood warming phase (removal of TNF-$\alpha$ and interleukin 1-$\beta$).

In view of their generally weakened conditions "acute" patients cannot be subjected to the intensive treatments which patients suffering from permanent renal insufficiency undergo: by virtue of the rapid modification of the internal liquid equilibria which it causes, a conventional haemodialysis or haemofiltration session, three times per week and lasting four hours, actually has the secondary effect of intense stressing of the cardiovascular system, which patients leaving the operating theatre could not as a general rule withstand.

In order to purify the blood of these patients and remove from them some of the water which accumulates in their tissues, recourse is therefore made to less intense but continuous treatments which are both well tolerated by the body because they involve no shock to the system and can be withstood by persons who are incapable of moving.

The subject of the present invention is therefore a multifunction device for extrarenal purification by extracorporeal circulation of blood, including a semipermeable separator component, characterized in that:

a) the separator component is active in adsorption and has at least one of the adsorption capacities below a1: adsorption of TNF-$\alpha$ greater than or equal to approximately 600 ng a2: adsorption of complement factor D greater than or equal to approximately 30 mg a3: adsorption of interleukin 1-$\beta$ greater than or equal to approximately 300 ng b) it has a urea clearance greater than or equal to approximately 20 ml/min for rates of blood flow, of dialysis liquid flow and of ultrafiltration equal respectively to approximately 100 ml/min, 33 ml/min and 0 ml/min, and in that c) it has an ultrafiltration coefficient in the presence of blood greater than approximately 5 ml/(h.mmHg).

d) the volume of compartment in the device intended for circulation of blood is less than or equal to approximately 150 ml.

The term "multifunction device" is intended to mean a device capable of simultaneously exercising at least one absorber function, a haemodialyser function and a haemofilter function.

The terms "adsorption" and "adsorb" are intended to mean diffusion-adsorption, where the interaction between the proteins and the polymer chains in the material of the separator component takes place just as well at the surface as in the bulk of the material.

The three adsorption capacities defined above correspond to the total quantity of TNF-α, complement factor D and/or interleukin 1-β which the separator component has adsorbed when it is saturated.

According to one characteristic of the invention, the semipermeable separator component of the device has at least two of the adsorption capacities defined above and, preferably, all three adsorption capacities a1, a2 and a3.

According to another characteristic of the invention, the separator component has, for increased efficiency, one or more adsorption capacity (capacities) greater than or equal to the following limit values:

a1: TNF-α adsorption greater than or equal to approximately 3000 ng a2: Factor D adsorption greater than or equal to approximately 90 mg, more preferably greater than or equal to approximately 150 mg a3: Interleukin 1-β adsorption greater than or equal to approximately 1500 ng.

A further subject of the invention is a multifunction device for extrarenal purification by extracorporeal circulation of blood, of the type including a bundle of hollow fibers, characterized in that:

a) the hollow fibers are composed of a homogeneous and symmetrical polyelectrolytic hydrogel derived from a copolymer of acrylonitrile and methallylsulphonate which contains approximately 3.3% (molar) of methallylsulphonate, and which is marketed by the company HOSPAL under the brand AN 69;

b) the total mass of hydrogel contains at least approximately 50 g of the said copolymer;

c) each fiber has an internal diameter of between approximately 180 and approximately 260 μm, and in that d) the volume of the blood compartment in the device is less than approximately 150 ml.

A further subject of the present invention is a hollow fiber useful for producing such a multifunction device for extrarenal purification by extracorporeal circulation of blood, this hollow fiber being characterized in that:

a) it has an internal diameter of between approximately 180 and approximately 260 μm;

b) it is composed of a homogeneous and symmetrical polyelectrolytic hydrogel;

c) it has a hydraulic permeability Lp greater than approximately 5 ml/h/mmHg/m$^2$;

d) it has a membrane resistance to urea less than approximately 200 min/cm, and in that e) it has the capacity to adsorb at least one of the substances chosen from TNF-α, complement factor D or interleukin 1-β and its linear adsorption capacity is, depending on the case, greater than approximately 125 pg/m for TNF-α, greater than approximately 6 μg/m, preferably greater than approximately 30 μg/m, for factor D and greater than approximately 60 pg/m for interleukin 1-β.

A detailed description will now be given of the device according to the invention and a type of hollow fibre which may constitute the separator component thereof.

The device according to the invention comprises two compartments separated by a separator component consisting of a flat sheet semipermeable membrane or of a bundle of semipermeable hollow fibers. This device is a multifunction device in that it can simultaneously exercise an adsorption function, defined by a capacity for adsorption of specific substances, a dialysis function, defined by a urea clearance, and an ultrafiltration function, defined by an ultrafiltration coefficient in the presence of blood.

The separator component is active in adsorption in that it itself has at least one of the above adsorption capacities a1 to a3. It is preferable for the said component to have at least two of the adsorption capacities in question.

Of course, it is advantageous for the separator component to have all three adsorption capacities a1 to a3 simultaneously.

For better efficiency, the separator component will have one or more adsorption capacity (capacities) greater than or equal to the following limit values:

a1: TNF-α adsorption greater than or equal to approximately 3000 ng a2: factor D adsorption greater than or equal to approximately 90 mg, more preferably greater than or equal to approximately 150 mg a3: interleukin 1-β adsorption greater than or equal to approximately 1500 ng.

The device also has a urea clearance greater than or equal to approximately 20 ml/min for rates of blood flow, of dialysis liquid flow and of ultrafiltration equal respectively to approximately 100 ml/min, 33 ml/min and 0 ml/min.

This clearance is specified for use of the device in the context of operation in continuous haemodialysis, in continuous arteriovenous haemodialysis (commonly denoted by CAVHD) or continuous venovenous haemodialysis (commonly denoted by CVVHD), for treatment of so-called "acute" patients. It indicates the purification efficiency of the device by diffusion of solutes from the blood towards the dialysate through the membrane and it is defined as the ratio of the solute flux to the concentration of the solute at the inlet to the device. It is determined in the context of an in vitro measurement protocol, in which the blood is replaced by a urea solution in the dialysate, the circulation of the fluids is carried out counter currentwise and with a temperature stabilized at 37° C. Its value is provided for operating conditions representative of those found in CAVHD or CVVHD, i.e. for a blood flow rate Qb of 100 ml/min, a dialysate flow rate Qd of 2 l/h and an ultrafiltration flow rate Qf of 0 ml/min.

The device has an ultrafiltration coefficient greater than approximately 5 ml/(h.mmHg).

The ultrafiltration coefficient is defined as being the ratio of the filtration rate Qf to the mean transmembrane pressure in the device, decreased by the oncotic pressure. The value provided is determined with blood circulating at 37° C. with a flow rate greater than or equal to 50 ml/min.

The ultrafiltration coefficient indicated makes it possible to extract approximately 1 l/h (1 liter/hour) of haemofiltrate at a transmembrane pressure of 200 mmHg.

The volume of the compartment in the device intended for circulation of blood is advantageously less than or equal to approximately 150 ml. This value is the limit assessed as being acceptable in view of the fact that it is generally assumed that the total extracorporeal volume should not exceed 250 ml.

A value of the order of 100 ml and, preferably, of the order of 80 ml is, of course, even more acceptable in this regard.

According to one embodiment of the device according to the invention, the separator component which is active in adsorption is made from a single type of material which is a homogeneous and symmetrical polyelectrolytic hydrogel in the form of a flat sheet membrane or a bundle of hollow fibers.

The hydrogel in question may be derived (1) from a copolymer of acrylonitrile and of at least one ionic or ionizable monomer, optionally including units originating from at least one other monomer containing olefinic unsaturation capable of being copolymerized with acrylonitrile, or (2) from a copolymer of acrylonitrile and of at least one ionic or ionizable monomer and of at least one non-ionic and non-ionizable monomer, or (3) from a mixture of copolymers defined under (1) and/or (2), or (4) from a mixture of at least one copolymer defined under (1) and/or (2) and of at least one copolymer of acrylonitrile and of at least one non-ionic and non-ionizable monomer, the ionic or ionizable monomer units representing from 1 to 80% (by mole) of the monomer units of one of the said copolymers and representing from 1 to 50% (by mole) of the monomer units in the final macromolecular compound.

Such macromolecular compounds as well as the various monomers which may be adopted as starting materials in their manufacture are more fully described in U.S. Pat. No. 4,545,910 regranted under No. Re. 34,239.

Among these macromolecular compounds, those defined under (1) above are preferred and, in particular, those for which the ionic or ionizable comonomer has olefinic unsaturation and carries anionic groups selected from sulphonate, carboxyl, phosphate, phosphonate and sulphate groups.

A particularly preferred monomer is sodium methallylsulphonate.

Among the monomers having olefinic unsaturation which can be copolymerized with acrylonitrile, alkyl acrylates, and in particular methyl acrylate, are preferred.

The hydrogel in question, which is non-crosslinked, may be manufactured according to the method described in European Patent No. 0,347,267.

Of course, the precise nature of the counter ion of the sulphonate groups in the hydrogel is not essential for correct operation of the device according to the invention: if the use of a hydrogel in completely acidic form is to be proscribed, it is possible for a part to be in acidic form and/or, in particular because of exchange with ions contained in the blood, such as potassium and calcium, for this type of counter ion to be present.

Use is advantageously made of a hydrogel derived from a copolymer of acrylonitrile and of methallylsulphonate which has an ionic capacity greater than or equal to 400 mEq/kg, and preferably greater than or equal to 500 mEq/kg (expressed with respect to dry polymer).

In the particular case in which use is made of a hydrogel derived from a copolymer of acrylonitrile and of methallylsulphonate which contains approximately 3.3% (molar) of methallylsulphonate and which is marketed by the company HOSPAL under the brand AN 69 (designated hereinbelow by "AN 69 hydrogel"), it has been demonstrated that the quantity of proteins adsorbed essentially depends on the mass of hydrogel present. It was possible to determine that this quantity should be at least approximately 50 g (expressed as dry polymer).

The separator component which is active in adsorption may be made, in a manner which is known per se, in the form of a flat sheet membrane or in the form of a bundle of hollow fibres.

The hollow fibers have an internal diameter of between approximately 180 and approximately 260 µm.

In the case in which these consist of a AN 69 hydrogel, their thickness will be between approximately 50 and approximately 250 µm.

In general, the thickness of the hollow fibers consisting of a homogeneous and symmetrical polyelectrolytic hydrogel may be between approximately 50 and approximately 250 µm. It will preferably be greater than 50 µm because, under these conditions, it will generally be possible to obtain an increase in the adsorption capacity for TNF-α and/or complement factor D and/or interleukin 1-β. As mentioned above, a further subject of the present invention is a hollow fiber useful for producing a multifunction device for extrarenal purification by extracorporeal circulation of blood. This hollow fiber has the following characteristics:

a) it has an internal diameter of between approximately 180 and approximately 260 µm;

b) it is composed of a homogeneous and symmetrical polyelectrolytic hydrogel;

c) it has a hydraulic permeability Lp greater than approximately 5 ml/h/mmHg/m$^2$;

d) it has a membrane resistance to urea less than approximately 200 min/cm, and in that e) it has the capacity to adsorb at least one of the substances chosen among TNF-α, factor D or interleukin 1-β and its linear adsorption capacity is, depending on the case, greater than approximately 125 pg/m for TNF-α, greater than approximately 6 µg/m, preferably greater than approximately 30 µg/m, for factor D and greater than approximately 60 pg/m for interleukin 1-β.

The hydraulic permeability Lp, one of the characteristic pasters of a given membrane, is defined as being the ratio of the filtration rate obtained per unit of surface area and transmembrane pressure; for the hollow fibers in question, the values of Lp are indicated for a dialysis bath at 37° C. It should be noted that when the hollow fibers have a developed surface area greater than 1 m$^2$, there is an approximate correspondence between the minimum ultrafiltration coefficient mentioned above and the minimum hydraulic permeability to the dialysis bath.

The membrane resistance to a solute is defined as the ratio, in steady state, of the difference in concentration on both side of the membrane to the solute flux passing through it in a purely diffusive mode. Direct measurement of the membrane resistance is made difficult by the unavoidable presence of transfer resistance of the parasitic boundary layers on the blood side and on the dialysis liquid side during a measurement of diffusive solute flux.

The value of the membrane resistance is estimated from the following measurements and considerations:

the clearance of a dialyser is measured in vitro, at zero ultrafiltration rate;

knowledge of the flow rates and the exchange surface area makes it possible to calculate the total transfer resistance of the device using the classical laws of a purely diffusive exchanger;

this total resistance constitutes an overestimate of the membrane resistance.

The homogeneous and symmetrical polyelectrolytic hydrogel of which the hollow fiber is composed is identical to that which was described above.

As regards the internal diameter, and optionally the thickness of the hollow fiber, the values indicated above are also applicable.

The examples below and the figures illustrate the invention.

EXAMPLES AND DETAILED DESCRIPTION OF THE DRAWINGS

Because of the difficulties inherent in in vivo tests, which can be carried out only in a hospital environment, and above all the risks which so-called "acute" patients might encounter if they were subjected to treatments employing defective devices, various in vitro determinations were carried out.

To this end, a model protein, cytochrome C, was chosen, the molecular weight (12 400) of which is close to cytokines (molecules of biological interest).

Examples 1 to 3 have the purpose of showing the relationship existing between the adsorption capacity of the membrane used and, respectively, the mass of copolymer contained in the membrane, the structure of the hydrogel of which the membrane is made and the nature of the copolymer.

Examples 4 to 6 respectively describe various hollow fibers and various products.

For examples 1 to 3, the operational protocol followed in order to acquire the adsorption capacity value in equilibrium with the concentration (Co) of a solution of a test molecule (cytochrome C) placed in contact with the hydrogels tested is as follows:

- the hydrogels tested are engaged in flat sheet membrane form or in hollow fiber form;
- the hydrogel sample is introduced into a container containing a volume Vo of test molecule solution at an initial concentration of Co. The solution is agitated.
- as a consequence of the adsorption process, the concentration of the test molecule in the container decreases. By means of assays and repeated additions of solution, the concentration of the test molecule in the container is repeatedly brought to the initial value Co, until a substantially constant concentration is obtained.
- the isothermal adsorption capacity for the test molecule of the hydrogels in question with respect to the mass of polymer Mp is then determined. The adsorbed quantity, determined on the basis of the total mass of the successive additions (M aj) can be calculated by the following relationship, derived from a mass balance equation:

isothermal adsorption capacity of the hydrogel $$Cads\ (G)\ iso=[Vo\cdot Co-Vf\cdot Cf+Maj]/Mp$$

where Vf is the final volume in the container and Cf the final test molecule concentration in the container.

Example 1

According to the protocol for acquiring the aforementioned adsorption isotherm, the adsorption capacities were evaluated for the following membranes consisting of AN 69 hydrogel:

- flat sheet membrane (1a) of 30 μm thickness;
- flat sheet membrane (1b) of 19 μm thickness;
- hollow fiber (1c) of 240 μm internal diameter and of 50 μm wall thickness;
- hollow fiber (1d) of 210 μm internal diameter and 42.5 μm wall thickness.

Preparation of Flat Sheet Membranes (1a) and (1b)

The starting liquid or collodion composition is composed of 20% by weight of AN 69 and 80% by weight of dimethylformamide (DMF). The flat sheet membranes (1a) and (1b) are obtained by phase inversion during pouring of this collodion onto a rotating drum, at 80° C. The dense film obtained is then subjected to stretching by three to three and a half times in water at 90°–96° C.

Preparation of the Hollow Fibers (1c) and (1d)

The fibers are obtained by a gelation method comprising the passage of a collodion composed of 35% by weight of AN 69, 52% by weight of DMF and 13% by weight of glycerol, heated to approximately 140° C., through a spinneret. The extrusion is carried out in the presence of an internal centering gas.

The fibers are subsequently subjected to an operation of stretching by four times at 95° C.

| Results of the adsorption tests | | | | |
|---|---|---|---|---|
| REF. | 1a | 1b | 1c | 1d |
| Cytochrome C solution concentration (mg/l) | 100 | 100 | 210 | 210 |
| Isothermal adsorption capacity Cads (G) iso (mg/g) | 110 | 113 | 595 | 555 |

For a given hydrogel structure, the quantity of protein adsorbed depends essentially on the mass of copolymer contained in the membrane.

AN 69 hydrogels of similar structure have identical adsorption properties if these properties are normalized with respect to polymer weight.

At identical polymer weight, it should be noted that the flat sheet membrane (1b) develops a surface area which is 1.6 times as large as that of the flat sheet membrane (1a) (thickness ratio) and the hollow fiber (1d) develops a surface area which is 1.2 times as great as that of the hollow fiber (1c). The adsorption process indeed took place in the bulk of the material and not at its apparent surface.

Example 2

This example illustrates the effect of the structure of the gel on the isothermal adsorption capacity of the hydrogel.

The structure of the gel depends on the manufacturing method used. Thus, the various methods mentioned above produce gels having structural variations (water content, organization of the polymer chains, density, etc.).

Materials Tested

- the flat sheet membrane (1a) described above;
- the hollow fiber (1c) described above;
- the AN 69 hollow fiber (2e) of internal diameter 425 μm and wall thickness 140 μm.

Preparation of the AN 69 Hollow Fiber (2e)

It is obtained by a conventional coagulation method involving:

- a colloid with 10% by weight of AN 69, 5% by weight of NaCl 9 g/l and 85% of dimethyl sulphoxide (DMSO), which is extruded at ambient temperature through a spinneret with diameter equal to 288 μm, the collodion distribution ring having diameters of 565 μm and 866 μm, at a drawing speed equal to 9 m/min;
- an internal coagulant liquid containing 9 g/l of NaCl;
- a reception tank filled with the same liquid as the internal coagulant;
- no stretching of the fiber;
- treatment of the fiber with a glycerol/water mixture (glycerol content greater than 60%) with a view to storing it and to subsequent manufacture of a device.

Result of the adsorption tests

| REF | 1a Flat sheet membrane | 1c Hollow fiber | 2e Hollow fiber |
|---|---|---|---|
| Concentration Co of the cytochrome C solution (mg/l) | 100 | 100 | 210 | 210 |
| Isothermal adsorption capacity Cads (G) iso (mg/g) | 110 | 140 | 595 | 685 |

Pairwise comparison of the materials 1a–1c and 1c–2e resulting from the same polymer but having fairly different structures [thus, hydrogel (1c) has a water content greater than that of hydrogel (1a)], shows that the adsorption capacity normalized with respect to the polymer mass can be modulated by the choice of the structure of the gel.

In addition to an effect on the kinetic parameters, the structure of the hydrogel may also modify the accessibility of the adsorption sites.

Example 3

In this example, the cytochrome C adsorption capacity of various hydrogels derived from copolymers of acrylonitrile and of sodium methallylsulphonate were determined, which hydrogels were in the form of balls, differing in their content of the latter monomer and, consequently, having different ionic capacities expressed in mEq/kg of polymer.

The hydrogel balls were obtained by a method of emulsion of a collodion composed of 10% by weight of polymer, 6.5% by weight of physiological saline solution (NaCl 9 g/l) and 83.5% by weight of DMF, this emulsifying step being followed by thermally reversible gelation from the ambient to −10° C.

The characteristics of the hydrogels tested (ionic capacity, water content) and the results of the tests of adsorption of a solution of 100 mg/l of cytochrome C are listed in the table below.

| Ionic capacity (mEq/kg) | 0 | 450 | 580 | 680 | 800 | 1130 |
|---|---|---|---|---|---|---|
| Water content (% by weight) | 85 | 78 | 78 | 82 | 83 | 90 |
| Cads (G) iso (mg/g) | 28 | 125 | 135 | 165 | 150 | 110 |

The adsorption capacity of the hydrogels can be modulated by the nature of the polymer according to a given adsorption objective with regard to a certain molecule.

Example 4

This example illustrates various hollow fibers obtained by a method of coagulation at ambient temperature, comprising the passage of a collodion, the nature of which is specified in table (N) below, through a spinneret of diameter d1, the collodion distribution ring having diameters d2 and d3; the diameters d1 to d3 defining the geometry of the spinneret are specified in the table in question; extrusion is carried out in the presence of an internal coagulant liquid, the composition of which appears in the aforementioned table, at a drawing speed which is also specified. In certain cases, the extrusion is carried out with the additional presence of an extractor tube producing external coagulation by means of a liquid which is identical to the internal coagulant. The fibers are received in a tank filled with this same liquid. The fibers are not stretched and, with a view to storing them and to subsequent manufacture of a device, they are glycerolated with a glycerol/water mixture (glycerol content greater than 60%).

The particular manufacturing conditions, as well as the characteristics of the fibers, are listed in Table (N) below.

TABLE (N)

| Ref. | 4f | 4g | 4b | 2e |
|---|---|---|---|---|
| Collodion | (1) | (1) | (1) | (2) |
| Coagulant | NaCl 9 g/l | NaCl 9 g/l | $Na_2HPO_4$ 9 g/l | NaCl 9 g/l |
| Extractor tube | yes | yes | no | no |
| Spinneret geometry d1/d2/d3 µm | 196/ 240/102 0 | 196/ 240/102 0 | 196/ 240/1020 | 288/ 565/866 |
| Drawing speed (m/min) | ≈8.3 | ≈9 | ≈9 | ≈9 |
| Internal diameter of the fibers (µm) | 200 | 240 | 250 | 425 |
| Wall thickness (µm) | 160 | 175 | 180 | 140 |
| Mass per unit length (mg/m) | | 66 | 52 | 44 |
| Lp ml/ (h.mmHg.m²)* | 16 | 16 | 23 | 130 |
| Urea membrane ** resistance (min/cm) | <110 | <50 | <65 | <55 |

(1): AN 69 18% and dimethylformamide 82%
(2): AN 69 10%, dimethyl sulphoxide 85%, sodium chloride 9 g/l solution 5%
(*): hydraulic permeability to the dialysis bath, at 37° C. carried out on mini filters having from 50 to 100 fibers.
(**): membrane resistance determined on mini filters with 50 to 100 fibers at blood flow rate Qb = 10 ml/min, at dialysate flow rate Qd = 20 ml/min and at zero ultrafiltration rate, total transfer resistance calculation constituting an overestimnte of the urea membrane resistance.

Example 5

Figure 1:
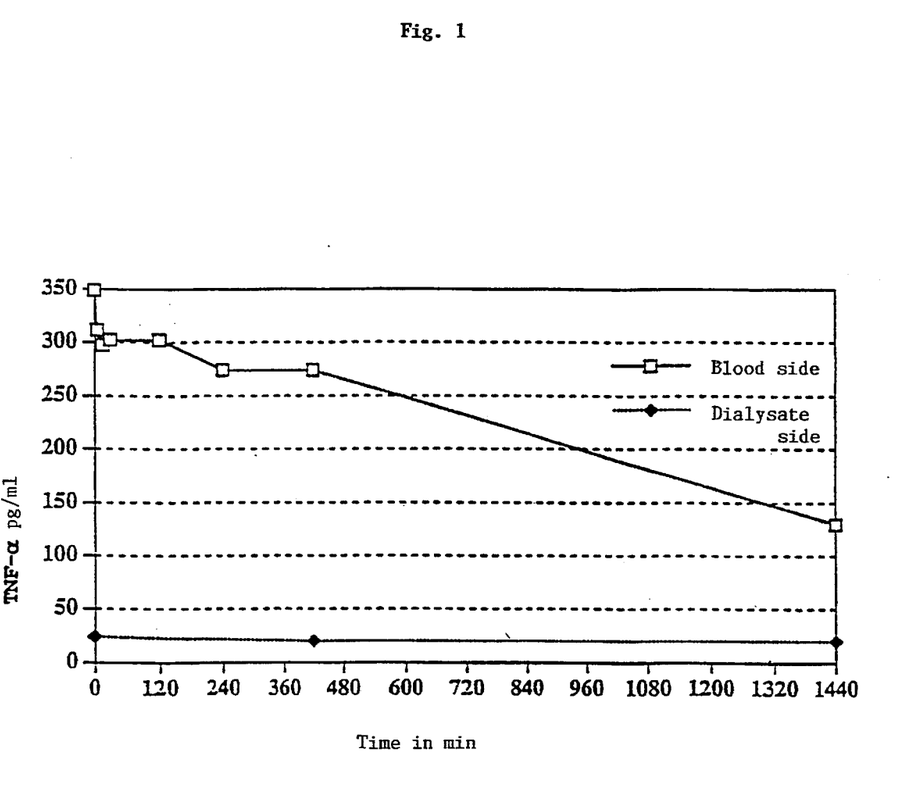
FIG. 1 illustrates the value of the concentration of TNF-α as a function of time under the conditions of Example 5.

The adsorption properties of a minidialyser including 140 fibers (4g) described in Example 4, of length 18 cm, were evaluated by closed-circuit circulation of human plasma loaded with TNF-α, the initial concentration (Co) of this protein being 350 pg/ml and the initial volume (Vo) of the plasma being 17.5 ml. No dialysis liquid circulation outside the fibers and no ultrafiltration were carried out. The evolution of the concentration (C) over time is shown by the attached FIG. 1. A minimum adsorption capacity for TNF-α of 2.3 ng per g of polymer can be deduced therefrom; for the fiber (4g) this corresponds to a linear adsorption capacity greater than or equal to 150 pg/m for TNF-α.

Example 6

The factor D adsorption capacity of the fiber (1c), described in Examples 1 and 2, measured in vivo, is greater than 4 mg/g of AN 69, that is to say greater than 56 µg/m of fibers.

Example 7

On the basis of the determinations which have just been explained, it is possible to define devices, the hollow fibers of which are similar to those used for producing the minidialyser which forms the subject of Example 5, the characteristics of which devices are indicated in the table below.

| Ref. | Mp (g) | BCV (ml) | Surface area (m²) | ultrafiltration coefficient (1) | Urea clearance (2) |
|---|---|---|---|---|---|
| 7a | 50 | 34 | 0.57 | 9 | >>25 |
| 7b | 90 | 62 | 1.03 | 16 | >>30 |
| 7c | 130 | 89 | 1.48 | 23 | >>32 |

Mp: mass of polymer
BCV: blood compartment volume
(1) in ml/(h.mmHg)
(2) in ml/min for rates of blood flow, of dialysis liquid and of ultrafiltration respectively equal to approximately 100 ml/min, 33 ml/min and 0 ml/min.

Example 8

Figure 2:
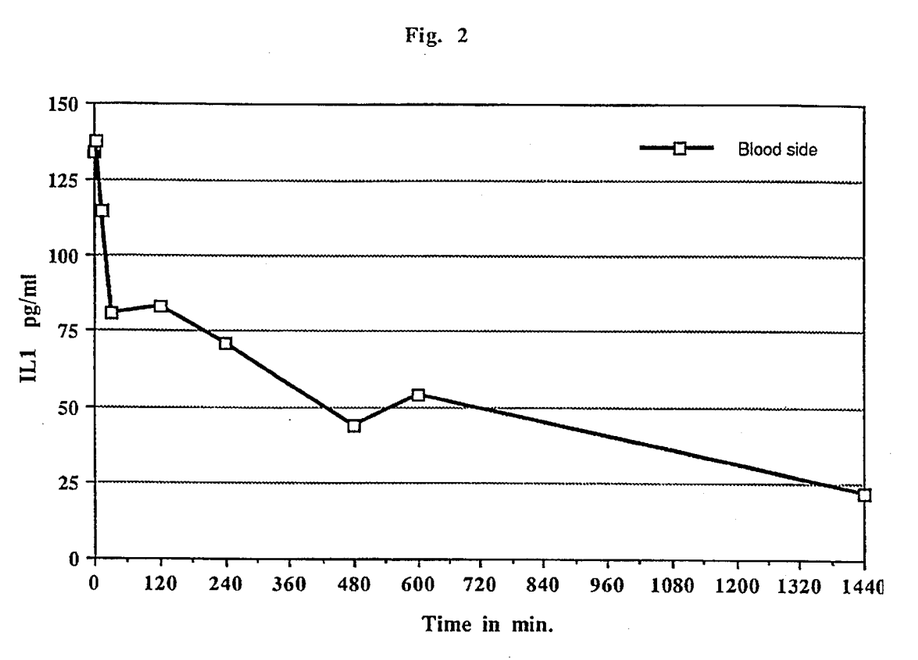
FIG. 2 illustrates the value of the concentration of interleukin 1-β (IL1) as a function of time under the conditions of Example 8.

The adsorption properties of a minidialyser including 170 fibers (1c) described in Example 1, of length 18 cm, were evaluated by closed-circuit circulation of human plasma loaded with interleukin 1-β, the initial concentration (Co) of this protein being 130 pg/ml and the initial volume (Vo) of the plasma being 20 ml. No dialysis liquid circulation outside the fibers and no ultrafiltration were carried out. The evolution of the concentration (C) over time is shown by the attached FIG. 2. A minimum adsorption capacity for interleukin 1-β of 4.8 pg per mg of polymer can be deduced therefrom, for the fiber (1c) this corresponds to a linear adsorption capacity greater than or equal to 67 pg/m of fibers for interleukin 1-β.

Example 9

Figure 3:
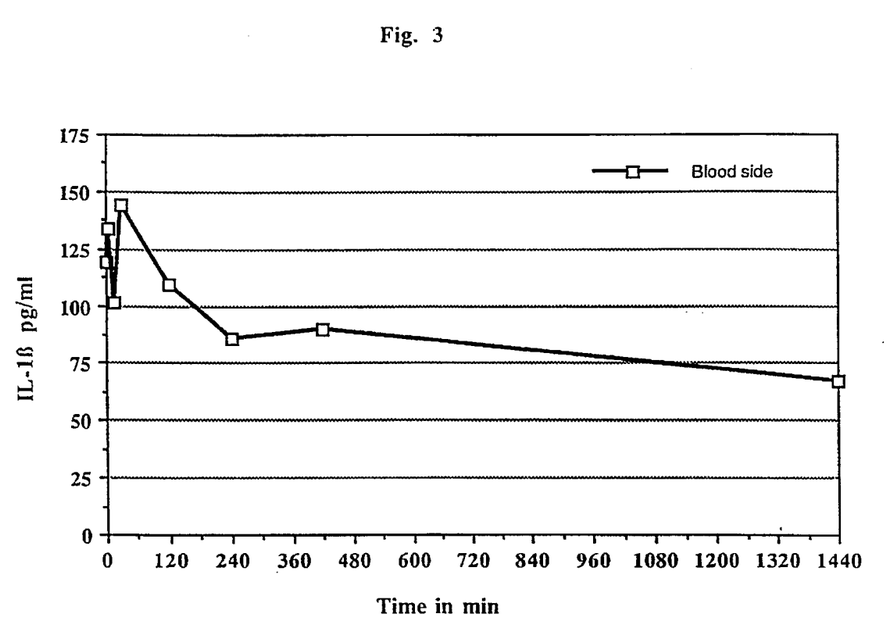
FIG. 3 illustrates the value of the concentration of interleukin 1-β (IL-1β) as a function of time under the conditions of Example 9.

The adsorption properties of a minidialyser including 70 fibers (4g) described in Example 4, of length 18 cm, were evaluated by closed-circuit circulation of human plasma loaded with interleukin 1-β, the initial concentration (Co) of this protein being 120 pg/ml and the initial volume (Vo) of the plasma being 20 ml. No dialysis liquid circulation outside the fibers and no ultrafiltration were carried out. The evolution of the concentration (C) over time is shown by the attached FIG. 3. A minimum adsorption capacity for interleukin 1-β of 1.15 pg/mg of polymer can be deduced therefrom; for the fiber (4g) this corresponds to a linear adsorption capacity greater than or equal to 75 pg/m of fibers for interleukin 1-β.

Finally, it should be noted that:

the adsorption capacities in examples 6, 8 and 9 are measured after 24 hours of tests, without waiting for saturation of the hollow fibers;

the experiments described in Examples 5, 6, 8 and 9 were carried out at concentrations of the substances to be adsorbed which were representative of the physiological values which may be reached during various pathologies, as the ones described above, on pages 2 and 3 of the present application.

I claim:

1. A multifunction device for extrarenal purification by extracorporeal circulation of blood, comprising a semipermeable separator component, wherein a) the separator component is active in adsorption and has at least one of the adsorption capacities below:

a1: adsorption of the TNF-α greater than or equal to approximately 600 ng;

a2: adsorption of the complement factor D greater than or equal to approximately 30 mg;

a3: adsorption of interleukin 1-β greater than or equal to approximately 300 ng;

b) the separator component has a urea clearance greater than or equal to approximately 20 ml/min for rates of blood flow, of dialysis liquid flow and of ultrafiltration equal respectively to approximately 100 ml/min, 33 ml/min and 0 m/min;

c) the separator component has an ultrafiltration coefficient in the presence of blood greater than approximately 5 ml/(h.mmHg); and d) the device contains a compartment for circulation of blood having a volume less than or equal to approximately 150 ml.

2. A device according to claim 1, comprising a separator component which is active in adsorption and has at least two of the adsorption capacities a1 to a3.

3. A device according to claim 2, comprising a separator component which is active in adsorption and has all the adsorption capacities a1 to a3.

4. A device according to claim 1, comprising a separator component which is active in adsorption and has a TNF-α adsorption capacity greater than or equal to approximately 3000 ng.

5. A device according to claim 1, comprising a separator component which is active in adsorption and has a factor D adsorption capacity greater than or equal to approximately 90 mg.

6. A device according to claim 1, comprising a separator component which is active in adsorption and has a factor D adsorption capacity greater than or equal to approximately 150 mg.

7. A device according to claim 1, comprising a separator component which is active in adsorption and has a interleukin 1-β adsorption capacity greater than or equal to approximately 1500 ng.

8. A device according to claim 1, comprising a separator component which is active in adsorption and is made from a single material which is a homogeneous and symmetrical polyelectrolytic hydrogel.

9. A device according to claim 8, wherein the hydrogel is derived from a copolymer of acrylonitrile and of at least one ionic or ionizable monomer, optionally including units originating from at least one other monomer containing olefinic unsaturation and capable of being copolymerized with acrylonitrile.

10. A device according to claim 8, wherein the hydrogel is derived from a copolymer of acrylonitrile and sodium methallylsulphonate.

11. A device according to claim 8, wherein the ionic capacity of the copolymer is greater than or equal to 400 mEq/kg.

12. A device according to claim 10, wherein the copolymer contains approximately 3.3% molar of sodium methallylsulphonate.

13. A device according to claim 12, wherein the quantity of hydrogel corresponds to at least approximately 50 g of dry copolymer.

14. A device according to claim 8, wherein the separator component which is active in adsorption is made in the form of a flat sheet membrane.

15. A device according to claim 8, wherein the separator component which is active in adsorption is made in the form of a bundle of hollow fibres.

16. A device according to claim 15, wherein the hollow fibers have an internal diameter of between 180 μm and 260 μm, inclusive.

17. A device according to claim 15, wherein the hollow fibers have an internal diameter of between 50 μm and 250 μm, inclusive.

18. A device according to claim 15, wherein the hollow fibers have a thickness of greater than 50 μm.

19. A device according to claim 8, wherein the ionic capacity of the copolymer is greater than or equal to 500 mEq/kg.

20. A device according to claim 19, wherein the copolymer contains approximately 3.3% molar of sodium methallylsulphonate.

21. A process for extrarenal purification by extracorporeal circulation of blood, comprising subjecting blood of a patient to circulation in a device in accordance with claim 1.

22. A multifunction device for extrarenal purification by extracorporeal circulation of blood, comprising a semipermeable separator component, wherein a) the separator component is active in adsorption and has at least one of the adsorption capacities below:

a1: adsorption of the TNF-α greater than or equal to approximately 600 ng;

a2: adsorption of the complement factor D greater than or equal to approximately 30 mg;

a3: adsorption of the interleukin 1-β greater than or equal to approximately 300 ng;

b) the separator component has a urea clearance greater than or equal to approximately 20 ml/min for rates of blood flow, of dialysis liquid flow and of ultrafiltration equal respectively to approximately 100 ml/min, 33 ml/min and 0 m/min;

c) the separator component has an ultrafiltration coefficient in the presence of blood greater than approximately 5 ml/(h.mmHg); and d) the device contains a compartment for circulation of blood having a volume less than or equal to approximately 150 ml;

said separator component comprising a hollow fiber having a) an internal diameter of between approximately 180 and approximately 260 μm;

b) the composition of a homogeneous and symmetrical polyelectrolytic hydrogel;

c) a hydraulic permeability Lp greater than approximately 5 ml/h/mmHg/m$^2$;

d) a membrane resistance to urea less than approximately 200 min/cm, and e) the capacity to adsorb at least one of THF-α, complement factor D or interleukin 1-β and a linear adsorption capacity is greater than approximately 125 pg/m for TNF-α, greater than approximately 6 μg/m for factor D or greater than approximately 60 pg/m for interleukin 1-β.

23. A device containing a hollow fiber according to claim 22, wherein the hydrogel is derived from a copolymer of acrylonitrile and of at least one ionic or ionizable monomer, optionally including units originating from at least one other monomer containing olefinic unsaturation and capable of being copolymerized with acrylonitrile.

24. A device containing a hollow fiber according to claim 22, wherein the hydrogel is derived from a copolymer of acrylonitrile and sodium methallylsulphonate.

25. A device containing a hollow fiber according to claim 23, wherein the copolymer contains approximately 3.3% molar of sodium methallylsulphonate, and is marketed by the company HOSPAL under the brand AN 69.

26. A device containing a hollow fiber according to claim 24, wherein the ionic capacity of the copolymer is greater than or equal to 500 mEq/kg.

27. A device containing a hollow fiber according to claim 24, wherein the ionic capacity of the copolymer is greater than or equal to 400 mEq/kg.

28. A device containing a hollow fiber according to claim 22, wherein the quantity of hydrogel corresponds to at least approximately 50 g of dry copolymer.

29. A process for extrarenal purification by extracorporeal circulation of blood, comprising subjecting blood of a patient to circulation in a device in accordance with claim 27.

* * * * *